United States Patent
Held et al.

(10) Patent No.: US 10,773,184 B2
(45) Date of Patent: Sep. 15, 2020

(54) EXTRACTION OF COMPOUNDS FROM CANNABIS

(71) Applicant: X Traxion, LLC, Chicago, IL (US)

(72) Inventors: Jeffery S. Held, Chicago, IL (US); Konstantin Stanis, Los Angeles, CA (US)

(73) Assignee: X TRAXION, LLC, Chicago, IL (US)

( * ) Notice: Subject to any disclaimer, the term of this patent is extended or adjusted under 35 U.S.C. 154(b) by 0 days.

(21) Appl. No.: 16/473,019

(22) PCT Filed: Dec. 26, 2017

(86) PCT No.: PCT/US2017/068396
§ 371 (c)(1),
(2) Date: Jun. 24, 2019

(87) PCT Pub. No.: WO2018/125857
PCT Pub. Date: Jul. 5, 2018

(65) Prior Publication Data
US 2019/0314739 A1    Oct. 17, 2019

Related U.S. Application Data

(60) Provisional application No. 62/440,961, filed on Dec. 30, 2016.

(51) Int. Cl.
*C07D 311/80* (2006.01)
*B01D 11/02* (2006.01)
*C07C 37/68* (2006.01)

(52) U.S. Cl.
CPC ........ *B01D 11/0211* (2013.01); *C07C 37/685* (2013.01); *C07D 311/80* (2013.01); *C07C 2601/16* (2017.05)

(58) Field of Classification Search
CPC . B01D 11/0211; C07D 311/80; C07C 37/685; C07C 2601/16
(Continued)

(56) References Cited

U.S. PATENT DOCUMENTS 6,344,349 B1    2/2002    Moldavsky
6,419,788 B1    7/2002    Wingerson
(Continued)

FOREIGN PATENT DOCUMENTS

EP    1385595 B1    5/2012
EP    1536810 B1    8/2012
(Continued)

OTHER PUBLICATIONS

UNODC, Recommended methods for the identification and analysis of cannabis and cannabis products, United Nations, New York, 2009, p. 1-60 (Year: 2009).*

(Continued)

*Primary Examiner* — Taylor V Oh
(74) *Attorney, Agent, or Firm* — Lempia Summerfield Katz LLC

(57) ABSTRACT

The disclosure provides embodiments processing and extracting compounds from cannabis. In one embodiment, the method includes providing a composition comprising the cannabis; inserting the composition into a treatment zone; applying a pulsed electric field to the composition within the treatment zone, wherein a portion of the cell membranes of the cannabis are lysed by electroporation to provide a product comprising a lysate; and separating at least a portion of a compound within the lysate from a remainder of the product.

24 Claims, 6 Drawing Sheets

(58) Field of Classification Search
USPC .......................................................... 549/390
See application file for complete search history.

(56) References Cited

U.S. PATENT DOCUMENTS

| | | | |
|---|---|---|---|
| 6,620,292 | B2 | 9/2003 | Wingerson |
| 6,630,507 | B1 | 10/2003 | Hampson |
| 7,600,707 | B2 | 10/2009 | Wingerson |
| 7,717,364 | B2 | 5/2010 | Wingerson |
| 8,136,747 | B2 | 3/2012 | Wingerson |
| 8,445,034 | B1 | 5/2013 | Coles, Jr. |
| 9,029,108 | B2 | 5/2015 | Kempkes |
| 2004/0049059 | A1 | 3/2004 | Mueller |
| 2008/0014627 | A1 | 1/2008 | Merchant |
| 2008/0029233 | A1 | 2/2008 | Wingerson |
| 2010/0119606 | A1 | 5/2010 | Whittle |
| 2011/0098348 | A1 | 4/2011 | De |
| 2012/0021481 | A1 | 1/2012 | Hebner |
| 2012/0184721 | A1 | 7/2012 | Wingerson |
| 2014/0004501 | A1 | 1/2014 | Talebpour |
| 2014/0044807 | A1 | 2/2014 | Bisterfeld Von Meer |
| 2014/0170721 | A1 | 6/2014 | Chin |
| 2016/0160229 | A1 | 6/2016 | Barrameda |

FOREIGN PATENT DOCUMENTS

| | | |
|---|---|---|
| WO | 2008019228 A2 | 2/2008 |
| WO | 2013165251 A1 | 11/2013 |
| WO | 2014164557 A1 | 10/2014 |

OTHER PUBLICATIONS

Teh et al ,The Use of Microwave and Pulsed Electric Field as a Pretreatment Step in Ultrasonic Extraction of Polyphenols from Defatted Hemp Seed Cake (*Cannabis sativa*) Using Response Surface Methodology, 7:3064-3076(Year: 2014).*

CBD is the Antidote to THC, www.NAIHC.org, Washington, Aug. 1, 2016; excerpt from the petition submitted to U.S. DEA asking "to remove industrial hemp from the federal drug schedules."

Cultivation Techniques Further Distinguish Industrial Hemp from Marijuana, www.NAIHC.org, Washington, Aug. 1, 2016; excerpt from the petition submitted to U.S. DEA asking "to remove industrial hemp from the federal drug schedules."

Devoss, David, The White-Collar Future of Weed, Playboy Magazine US Magazine; Nov. 2016.

Ethanol as a Solvent, EasyChem, Mar. 1, 2016; retrieved on Feb. 21, 2018 from https://web.archive.org/web/20160301023528/http://www.easychem.eom.au/production-ofmaterials/renewable-ethanol/ethanol-as-a-solvent.

Industrial-Grade Pulsed Electric Field (PEF) System, PowerMod™, 2012 Diversified Technologies, Inc.

ISR and Written Opinion 03132018, International Search Report and Written Opinion cited in the corresponding International App No. PCT/US17/68396; dated Mar. 13, 2018; 10pp.

Pataro, G. et al., Extraction of Valuable Compounds From Microalgae by Pulsed Electric Fields and High Pressure CO2, https://www.researchgate.net/publication/311439886; Nov. 2016; DOI: 10.13140/RG.2.2.21008.81925.

Teh, Sue-Siang et al., The Use of Microwave and Pulsed Electric Field as a Pretreatment Step in Ultrasonic Extraction of Polyphenols from Defatted Hemp Seed Cake (*Cannabis sativa*) Using Response Surface Methodology, Food Bioprocess Technol (2014) 7:3064-3076; DOI 10.1007/s11947-014-1313-y.

The PureHemp Biorefinery Technology, 2017 PureHemp Technology, https://purehemptech.com/technology/; retrieved from internet on Jan. 19, 2017.

Vega-Mercado, Humberto et al., Pulsed Electric Fields in Food Preservation, 2007 by Taylor & Francis Group, LLC; pp. 783-813.

Hidenori Akiyama et al., Bioelectrics, Chapter 6: Environmental Applications, Food and Biomass Processing by Pulsed Electric Fields; DOI 10.1007/978-4-431-56095-1; Springer Japan 2017; 92 pp.

* cited by examiner

EXTRACTION OF COMPOUNDS FROM CANNABIS

CROSS-REFERENCE TO RELATED APPLICATIONS

The present patent document is a § 371 nationalization of PCT Application Serial Number PCT/US2017/068396, filed Dec. 26, 2017, designating the United States, which is hereby incorporated by reference, and this patent document also claims the benefit of U.S. Provisional Patent Application No. 62/440,961, filed on Dec. 30, 2016, which is hereby incorporated by reference in its entirety.

FIELD

The following disclosure relates to the extraction of compounds from cannabis. Specifically, the following disclosure relates to the extraction of compounds from cannabis using a pulsed electric field (PEF).

BACKGROUND

In order to extract various compounds from cannabis, the process requires the breaking down, or "lysis," of the cell membranes of the plant material to release compounds such as cannabidiol (CBD), tetrahydrocannabinol (THC), or terpenes, and/or other compounds stored therein. Following the lysis of the cell membranes, the released compounds are further processed and/or isolated from one another. Conventional methods of lysing the cells and extracting certain compounds include using hexane, benzene, butane, chloroform, supercritical fluid $CO_2$, or other solvents. These methods also require drying of the material prior to extraction. These processes are slow, expensive, difficult to perform in a continuous flow process, and/or use dangerous and toxic materials.

Therefore, it is desirable to provide improved devices, systems, and methods for breaking down the cell membranes of the cannabis and extracting and/or purifying selected compounds.

SUMMARY

The disclosure provides embodiments for separating compounds using a pulsed electric field. In one embodiment, the method includes providing a composition comprising the cannabis; inserting the composition into a treatment zone; applying a pulsed electric field to the composition within the treatment zone, wherein a portion of the cell membranes of the cannabis are lysed by electroporation to provide a product comprising a lysate; and separating at least a portion of a compound within the lysate from a remainder of the product.

BRIEF DESCRIPTION OF THE DRAWINGS

Exemplary embodiments are described herein with reference to the following drawings.

DETAILED DESCRIPTION

Figure 1:
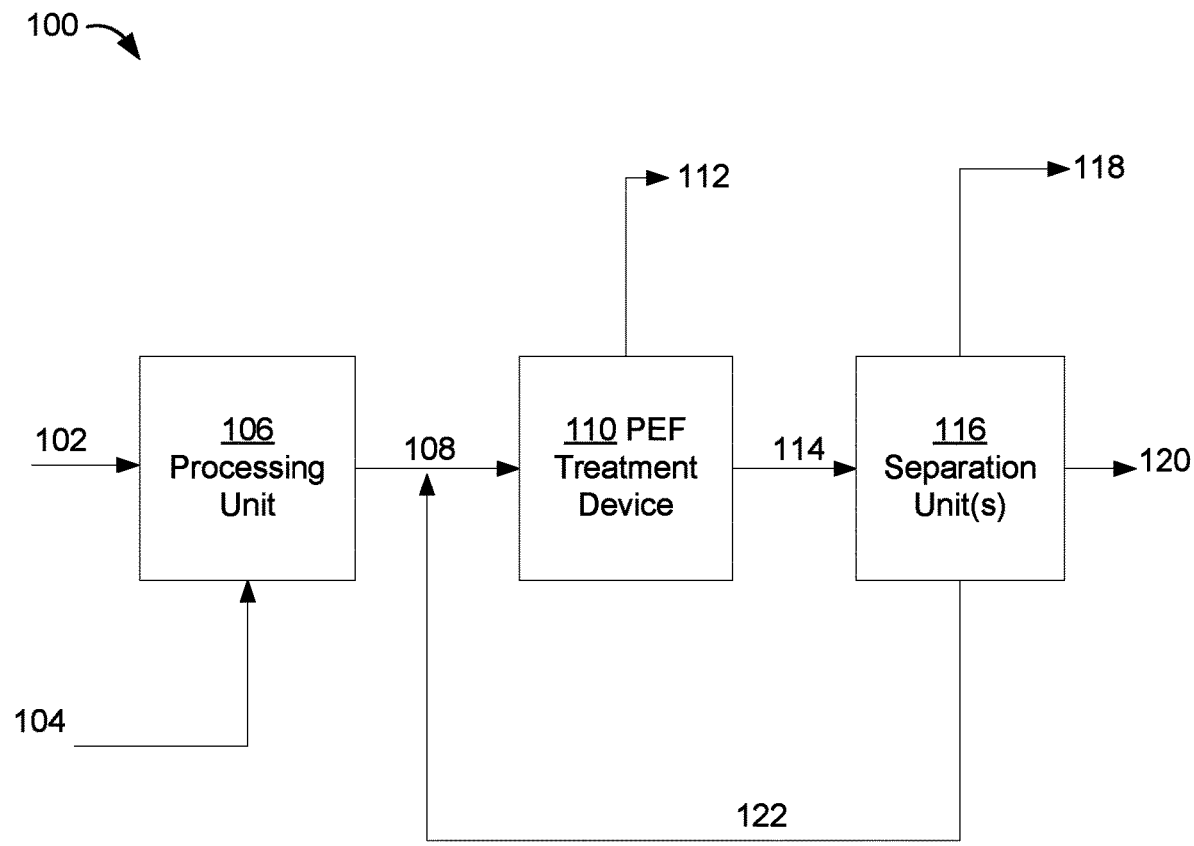
FIG. 1 depicts a schematic diagram of a process of extracting compounds from cannabis according to one example.

As described in further detail below, methods, devices, and systems are provided for processing cannabis to separate and/or purify certain compounds from the starting composition. The methods, devices, and systems include breaking down the cell walls of the cannabis by using a pulsed electric field (PEF). The PEF may be advantageous in isolating one or more compounds of the plant (e.g., the CBD, THC, or terpenes) in a more efficient and cost-effective manner.

Definitions

As used here, the term "cannabis" may refer to the genus of the flowering plant that includes three species (i.e., *Cannabis sativa, Cannabis indica*, and *Cannabis ruderalis*). In some examples, cannabis may refer to a portion or structure of the flowering plant, such as the cola, calyx, pistil, and/or trichome. In certain examples, cannabis includes the fiber of the cannabis plant (i.e., hemp).

As used herein, the term "pulsed electric field" or "PEF" may refer to a non-thermal processing technique using short pulses (e.g., microsecond to millisecond scale), with a field strength sufficient to affect the cells within the plant tissue (e.g., greater than 100 V/cm). The pulses induce poration of plant, animal, or microbial cells, leading to cell lysis, also known as electroporation. This process may be advantageous in providing a targeted, flexible, energy-efficient, and/or time-efficient separation technique.

As used herein, the term "electroporation" may refer to the process of applying an electric field to cells in order to (e.g., irreversibly) lyse the cell membrane.

As used herein, the term "lysis" may refer to the breaking down of the membrane of a cell.

As used herein, the term "lysate" may refer to the composition or solution containing the cells and the intracellular material contained therein, wherein at least a portion of the material is not contained within the membrane.

As used herein, the term "treatment zone" may refer to the physical volume(s) in which the electric field is applied to the composition (e.g., slurry composition).

As used herein, the term "slurry" or "slurry composition" may refer to a fluid mixture including whole, crushed, ground, or pulverized plant material and a liquid. In some examples, the slurry composition is the cannabis plant or a portion of the cannabis (e.g., the trichomes of the plant) and water from the plant itself that has been released upon crushing, grinding, or pulverizing the plant. In other examples, water may be added to the whole, crushed, or pulverized cannabis plant (or a portion thereof) to provide the slurry composition. In yet other examples, a solvent may be added to the whole, crushed or pulverized cannabis plant (or a portion thereof) to provide the slurry composition.

As used herein, the term "batch process" may refer to a technique in which an electric field is applied to a static volume of material (e.g., slurry composition).

As used herein, the term "continuous flow" may refer to a flow production method to produce or process materials without interruption. In other words, the materials (e.g., slurry) that are being processed are continuously in motion.

Process of Separating Compounds from Cannabis

FIG. 1 depicts a schematic diagram of a process 100 of separating compounds from cannabis. The process 100 includes forming the cannabis-based composition to undergo processing by a pulsed electric field.

Providing Cannabis-Based Composition

As depicted in FIG. 1, the exemplary process 100 of forming the composition may include providing cannabis 102 and an optional liquid stream 104 to a processing unit 106 (e.g., slurry formation vessel). The processing unit 106 may be any open or closed vessel capable of receiving the cannabis 102 and optional liquid stream 104, and forming a slurry.

The cannabis 102 may be whole, crushed, ground, or pulverized within the processing unit 106 to form a slurry composition 108. As noted above, water from the cannabis 102 may be extracted during the process to assist in forming the slurry composition.

The process of crushing the cannabis may include inserting the cannabis plant between two rollers spaced a predetermined distance from each other and moving in opposite directions from each other at a predetermined rate and pressure. Alternatively, the cannabis plant may be chopped, macerated, crushed or pulverized, e.g., within a blender having a blade rotating at a predetermined rate. In another example, the cannabis plant may be crushed by compressing the plant within a confined space at a predetermined pressure.

As noted below, the process of crushing the cannabis may occur at the same time as subjecting the cannabis to the pulsed electric field. For example, the cannabis may be inserted between rollers while the pulsed electric field is applied to the rollers (e.g., the rollers themselves act as electrodes).

In some examples, an optional liquid stream 104 is added to the cannabis to assist in forming the processed cannabis (e.g., slurry) composition 108. The optional liquid stream 104 may be or include water. Additionally, or alternatively, the optional liquid stream 104 may be or include a solvent. In certain examples, the cannabis 102 may be soaked in the water or solvent for a predefined amount of time prior to the PEF treatment. The soaking time may be in a range of 1 minute-24 hours, 30 minutes-12 hours, or 1-6 hours. The solvent may be an organic or inorganic solvent. In some examples, the solvent includes benzene, hexane, butane, ethanol, isopropyl alcohol, butyl alcohol, ethyl acetate, and/or acetone. In one particular example, the solvent is ethanol.

The plant material to liquid weight percent ratio or moisture content within the slurry may be varied based on the desired properties of the slurry composition. In some examples, the plant material to liquid weight percent ratio is from 10:90 to 90:10 plant material to liquids, 20:80 to 80:20, 30:70 to 70:30, 40:60 to 60:40 or approximately 50:50. In other examples, the moisture content is from 10-90 wt. %, 20-80 wt. %, 30-70 wt. %, 40-60 wt. %, or about 50 wt. %. In some examples, the plant to liquid weight percent ratio or moisture content is adjusted to a predefined ratio or moisture level to assist in improving the subsequent processing and extraction. In some examples, the plant to liquid weight percent ratio or moisture level is adjusted by drying the cannabis 102 or slurry composition 108. In other examples, the plant to liquid weight percent ratio or moisture level is adjusted by soaking the cannabis 102 in water or a solvent.

In some examples, the cannabis 102 may be pre-processed prior to insertion into the processing unit 106. For example, a portion of the cannabis plant may be separated from the rest of the plant prior to insertion into the processing unit 106. This may be advantageous in selecting a portion of the plant that has a higher concentration of a desired compound (e.g., the CBD or THC) for downstream separation. The cola, calyx, pistil, and/or trichomes of the plant may be separated from the remainder of the plant for processing in the processing unit 106.

In some examples, at least a portion of the flower buds from the cannabis plant may be removed from the remainder of the plant. In one example, the trichomes of the cannabis plant are separated from the remainder of the plant to form the cannabis composition 102 introduced into the processing unit 106. In some examples, the trichomes are separated by chilling or freezing the cannabis plant, and subsequently shaking or vibrating the chilled or frozen plant. The temperature of the plant may be reduced from ambient temperature conditions (e.g., 20-25° C.) to temperatures at or lower than 15° C., 10° C., 5° C., 0° C., or −5° C., for example. Such a process is advantageous in hardening the plant and making it easier to remove the trichomes from the remainder of the cannabis plant by agitating the chilled or frozen plant.

Inserting Cannabis into Treatment Zone

As depicted in FIG. 1, following processing of the cannabis into a crushed composition (e.g., a slurry composition), the processed cannabis composition 108 is inserted into a treatment zone of a pulsed electric field (PEF) treatment device 110.

In some examples, the cannabis is processed in to a crushed or slurry composition at a same time that the cannabis is subjected to the pulsed electric field. For instance, a pulsed electric field may be applied as the cannabis passes through rollers, wherein the rollers both crush the cannabis and act as electrodes in the PEF process.

The processed composition 108 may be inserted into the PEF treatment device 110 in a batch process. For example, the processed cannabis composition 108 may be (e.g., manually) removed from the processing unit 106 and placed within a vessel of the treatment zone 110. After processing within the PEF treatment device 110, the batch may be removed and transferred to the separation units 116. Another batch may then be inserted into the PEF treatment device 110, and the process may be repeated one or more times.

Alternatively, in certain examples, the processed cannabis composition 108 may be inserted into the treatment zone 110 in a continuous flow process. For example, the processed cannabis composition 108 may be transported or pumped from the processing unit 106 to the treatment zone 110 at a specified rate. The specified rate may be adjusted based on the properties of the processed composition and treatment zone. As noted above, the continuous flow process may include moving the composition between rollers to both crush the plant composition and subject the composition to a PEF treatment.

Application of Pulsed Electric Field

Within one or more treatment zones of the PEF treatment device 110, the cannabis composition 108 is subjected to a pulsed electric field, wherein a portion of the cell membranes of the cannabis are lysed by electroporation. This process results in product having a lysate.

The PEF treatment device uses short (e.g., microsecond or millisecond) pulses and a specialized treatment chamber or zone to disrupt cell membranes in a process called electroporation to lyse the cannabis cell walls. The pulsed electric fields expand existing pores within the cell membranes of the cannabis until they rupture, or lyse, opening the cells to the surrounding solution through electroporation.

This is believed to occur due to migration of ions towards the membrane of the cells, causing an enhanced electric field to cross the membrane resulting in growth of pores in the cell membranes.

In some examples, the PEF treatment device includes a single treatment chamber or zone. In other examples, the PEF treatment device includes a plurality of treatment chambers. In other examples, the PEF treatment device may include at least two rollers, which compress the cannabis and serve as electrodes, where the distance between two rollers includes the treatment zone. Certain example of PEF treatment device and systems are discussed in greater detail below with reference to FIGS. 2-5. Additional details of PEF treatment are disclosed in U.S. Pat. No. 5,690,978, which is incorporated by reference herein in its entirety.

Various parameters may be adjusted within the PEF treatment device 110 to optimize the lysing of the cannabis cell walls in a time-efficient and cost-effective manner. One or more following variables may be adjusted to optimize the lysing of the cell walls: (1) the water or solvent content of the cannabis composition entering the PEF treatment device; (2) the components or make-up of the cannabis composition itself (e.g., the strain of cannabis or the make-up of the pre-processed portion of the cannabis plant being inserted, or the time since harvest of the cannabis make affect the make-up composition); (3) the temperature of the cannabis composition entering the PEF treatment device; (4) the field strength of the pulsed electric field applied to the cannabis composition; (5) the total duration of the pulsed electric field applied whether in a single pulse or multiple, shorter pulses, (6) the flow rate or treatment time for the cannabis composition within the PEF treatment device, and/or (7) the conductivity of the cannabis composition.

A critical electric field, $E_{CRIT}$, needs to be exceeded for a given total time for electroporation to reliably occur across a population of cells of the slurry of cannabis. $E_{CRIT}$ may be directly related to the size of the cells to be electroporated. The electric field should be minimized, since the cost depends on the square of the electric field. Below $E_{CRIT}$, cells are not electroporated, independent of the pulse duration. Above $E_{CRIT}$, the total energy, which scales as the square of the field strength, and directly with treatment time, may be minimized.

The conductivity of the slurry may also be minimized. Conductivity is a function of ions contained in the slurry of cannabis. The fluid conductivity of cannabis composition may determine how much current flows through cannabis composition when the pulse electric fields are applied to treatment zone. This provides how much energy will be used in applying the pulsed electric fields.

In one example, an optimal field strength or magnitude of the pulsed electric field, an optimal pulse duration, and/or an optimal flow rate for a continuous flow process may be calculated based on the multiple variables of the cannabis composition (e.g., the water content, the inlet temperature, and the cannabis make-up). In another example, the water content or inlet temperature may be optimized to provide a cannabis composition suitable for a specific field strength, pulse duration, and/or flow rate. In yet another example, the flow rate of the slurry composition into or out of the PEF treatment device may be monitored, and the pulse duration and/or the frequency may be adjusted based on the measured flow rate. In other words, based on certain known properties for operation of the PEF treatment device, other properties may be adjusted to optimize the lysing process.

In certain examples, the optimization involves choosing the magnitude of the pulsed electric fields to lyse the cell membranes of the cannabis with the lowest energy applied. In other words, the magnitude of the pulsed electric fields to lyse the cell membranes of cannabis of a predetermined size may be chosen to minimize energy consumption while achieving the desired level of lysing of the cells in the slurry. The pulsed electric field may have a field strength or magnitude of at least 100 V/cm, at least 1 kV/cm, in a range of 1 kV/cm to 10 kV/cm, in a range of 3 kV/cm to 10 kV/cm, or in a range of 500 V/cm to 5 kV/cm.

In other examples, the frequency of the pulse electric fields may be adjusted in proportion to the flow of the slurry of cannabis to achieve an applied energy of 1 to 300 kJ/liter, depending on the applied voltage, required treatment time, and conductivity of the slurry. The adjustment may be automatic.

The pulse duration of the pulse electric fields may be in a range of 0.1 microsecond (µs) to 10 milliseconds (ms), or in a range of 1 µs to 1 ms. In one example, the pulsed electric field has a magnitude in a range of 500 V/cm to 5 kV/cm and a pulse duration in a range of 1 µs to 1 ms. Multiple pulses may be applied as the material passes through the treatment zone to achieve a total treatment time.

In some examples, the slurry composition is inserted at a flow rate of at least 1 liter/hour, or in a range of 10 liters/hour to 100,000 liters/hour.

As noted above, the water content of the cannabis composition entering the PEF treatment device may be 10 wt. %, 20 wt. %, 30 wt. %, 40 wt. %, 50 wt. %, 60 wt. %, 70 wt. %, 80 wt. %, or 90 wt. %.

The temperature of the cannabis composition entering the PEF treatment device is also variable. The initial temperature may be 10° C., 15° C., 20° C., 25° C., 30° C., 35° C., 40° C., 50° C., 60° C., 70° C., 80° C., or 90° C.

Separation of Compounds from Lysed Product

Following lysing of at least a portion of the cannabis composition using PEF, the products may be separated from each other. This may be advantageous in isolating a specific compound or purifying one or more compounds of the cannabis composition.

In certain examples, the downstream separation of products following application of the PEF may occur immediately following the PEF treatment. In alternative examples, a delay or period of time may exist between PEF treatment and downstream processing/separation. The period of time may be in a range from 1 minute-24 hours, 30 minutes-12 hours, or 1-6 hours.

As depicted in FIG. 1, a portion of the products may be separated into two PEF treatment product streams 112 and 114. One of the product streams 114 is sent to the separation unit(s) 116. The other product stream 112 may represent a waste or recycle stream. For example, the product stream 112 may be unreacted or unlysed crushed cannabis that may be discarded or recycled back to the processing unit 106 or back to the PEF treatment device 110 with the slurry composition 108.

In another alternative example, the product exiting the PEF treatment device is sent in a single product stream to the separation unit(s) 116 without any discard or recycle prior to the separation unit(s) 116.

In another alternative example, the product exiting the PEF treatment device is separated into a liquid and solid compositions or streams and sent to the separation unit(s) 116 for differing extractions on each composition or stream.

The separation unit(s) may include a single unit configured to separate at least a portion of one compound from the remainder of the PEF treatment product stream 114. In other examples, the separation unit(s) 116 include a plurality of units configured to separate a plurality of compounds from each other.

The separation unit(s) 116 may include filtration units, distillation columns, crystallization units, adsorption units, evaporation units, refining units, centrifugation units, liquid-liquid extraction units, sublimation units, and/or other types of separation units known in the art.

The separation unit 116 may include a first distillation column. The first distillation column may be a fractionating column having a predetermined number of trays or plates within the column. The distillation column may be configured to separate a majority of the THC (having a boiling point at 157° C.) from the top of the distillation column from the CBD and other compounds having higher boiling points. CBD has a boiling point in the range of 160-180° C. and terpenes having boiling points ranging between 119-224° C.

In other words, the lighter end compound, THC, may be separated off the top of the distillation column in a THC-rich product stream 118. This process may produce a THC-rich product stream having 80 wt. %, 90 wt. %, 95 wt. %, 99 wt. %, 99.5 wt. %, or 99.9 wt. % THC within the THC-rich product stream 118. (The THC-rich product stream 118 may also include certain compounds like α-pinene, β-sitosterol, β-caryophyllene, and cannabigerol (CBG), which have lighter boiling points than THC.

In some examples, a side-stream may be produced from the single distillation column.

In other examples, a second distillation column may be provided to further process the products separated from the top of the first distillation column (e.g., within the THC-rich product stream). Alternatively, the second distillation column may be provided to further process the products separated from the bottom of the first distillation column (e.g., within the THC-deficient product stream). For example, the second distillation column may be configured to create a CBD-rich product stream 120 by separating a majority of the CBD off the top of the second distillation column from the remaining compounds in the THC-deficient product stream. This process may produce a CBD-rich product stream 120 having 80 wt. %, 90 wt. %, 95 wt. %, 99 wt. %, 99.5 wt. %, or 99.9 wt. % CBD within the CBD-rich product stream 118.

The bottoms from the second distillation column may include a terpene-rich stream. This terpene-rich product stream may have 80 wt. %, 90 wt. %, 95 wt. %, 99 wt. %, 99.5 wt. %, or 99.9 wt. % terpenes.

In some examples, the bottoms from the second distillation column could be sent to a third column for further processing. In certain examples, the bottoms from the first or second distillation column could be recycled back as a recycle stream 122 to the PEF treatment device or processing unit 106 for further processing.

Figure 2:
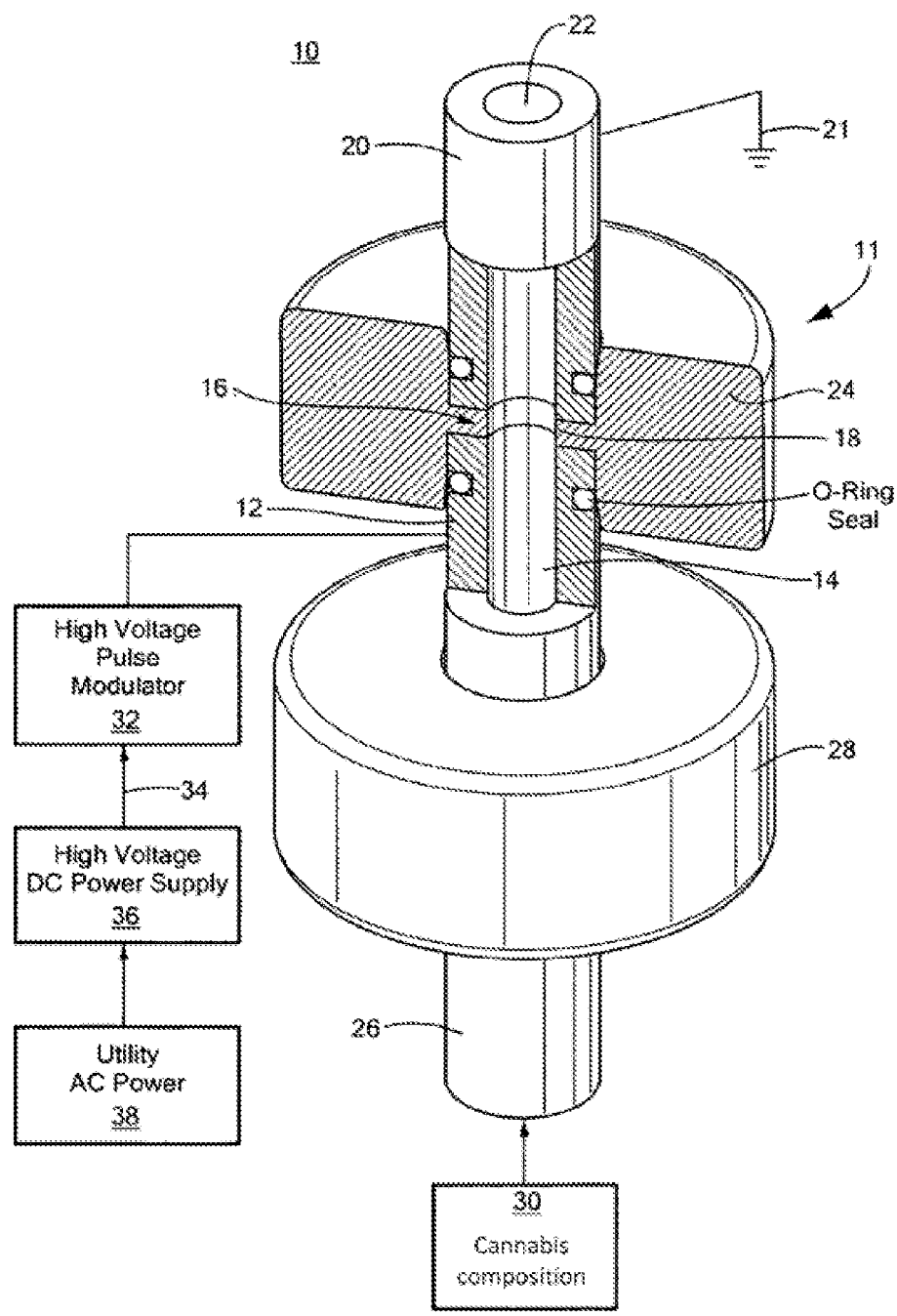
FIG. 2 depicts an example of a PEF treatment device configured for continuous extraction of various compounds from cannabis.

FIG. 2 depicts an example of a pulsed electric field (PEF) system 10 that may be used to lyse the cannabis composition 30. FIG. 2 depicts one-half of PEF treatment chamber 11 of the PEF system 10, which includes a high voltage electrode 12 with a channel 14, a treatment zone 16 with a channel 18, a ground electrode 20 with an outlet 22, and an insulator 24 between the high voltage electrode 12 and the ground electrode 20. The high voltage electrode 12 is in communication with a high voltage pulse modulator 32. The high voltage pulse modulator 32 may receive high voltage DC by a line 34 from the high voltage DC supply 36 coupled to the utility AC power 38. The ground electrode 20 is connected to the ground 21. Additional details of the structure and operation of the treatment chamber 11 are disclosed in U.S. Pat. No. 5,690,978, which is incorporated by reference herein in its entirety.

The other half of PEF treatment chamber 11 may include at least one additional treatment zone (not depicted) located between the ground electrode 26, the insulator 28, and the high voltage electrode 12, each having a similar structure and connection to high voltage pulse modulator 32 as discussed above. The single high voltage electrode 12 faces the two grounded electrodes 22, 26 (one on each side), producing two areas with electric fields. The system 10 may include one or more treatment chambers. In one example, the system 10 includes two PEF treatment chambers each having two treatment zones therein, (e.g., discussed in greater detail in FIG. 3 below). Other implementations of the treatment chambers may include parallel plates or co-linear electrodes to apply the high voltage pulses across the cannabis composition 30 (e.g., slurry composition).

As depicted in FIG. 2, the cannabis composition is continuously fed into the channel 14 of the high voltage electrode 12. High voltage pulsed signals generated by the high voltage pulse modulator 32 are applied to high voltage electrode 12 to create an electric field in treatment zone 16. Due to the physical configuration of the high voltage electrode 12, the ground electrode 20, and the insulator 24, a uniform or substantially uniform electric field is present in the treatment zone. The electric field in the treatment zone 16 has a vector direction pointing from the high voltage electrode 16 to the ground electrode 20. Therefore, as the continuous flow of the slurry of cannabis 30 passes through the channel 14 in the high voltage electrode 12, to the channel 18 in the treatment zone 16, and then to the outlet 22 in the ground electrode 20, the slurry of cannabis 30 is subject to an applied electric field that is concentrated in treatment zone 16. This causes the cell membranes of cannabis to lyse and release the CBD, THC, and terpene compounds, as well as other compounds therein. The solution of lysed cells, partially lysed cells, unlysed cells, exits via the port 22 for additional processing to create the final products.

In one example, the high voltage power supply 36 is a high frequency switching supply. In this design, input utility AC power 38 may be rectified and "chopped" at high frequencies, e.g., about 10 to about 50 kHz, then passed to a transformer rectifier. The DC power supply 36 may provide highly regulated and rapidly adjustable output voltage which supports tight control of the PEF process parameters. In one example, the DC power supply 36 may be used in applications of up to 500 kW, which supports PEF processing at flow rates up to 100,000 liters/hr.

The high voltage pulse modulator 32 depicted in FIG. 2 is configured to transform the average power output by the high voltage DC power supply 36 into short, high-power pulses. The high voltage pulse modulator 32 may use a "hard switch" that may directly switch full voltage. The high voltage pulse modulator 32 may also have a low impedance to provide consistent output voltage over a range of peak currents required as the fluid conductivity of slurry of cannabis 30 varies. Additionally, the high voltage pulse modulator 32 may be a solid-state, high-voltage modulator, e.g., as disclosed in U.S. Pat. Nos. 5,440,610 and 6,900,557, herein incorporated by reference in their entireties. Other high voltage pulse modulator topologies are known to those skilled in the art and may be used as well. The desired elements of the pulse modulator are fast pulse rise times, adjustable pulse width and frequency, and consistent pulse voltages when the product conductivity changes.

Figure 3:
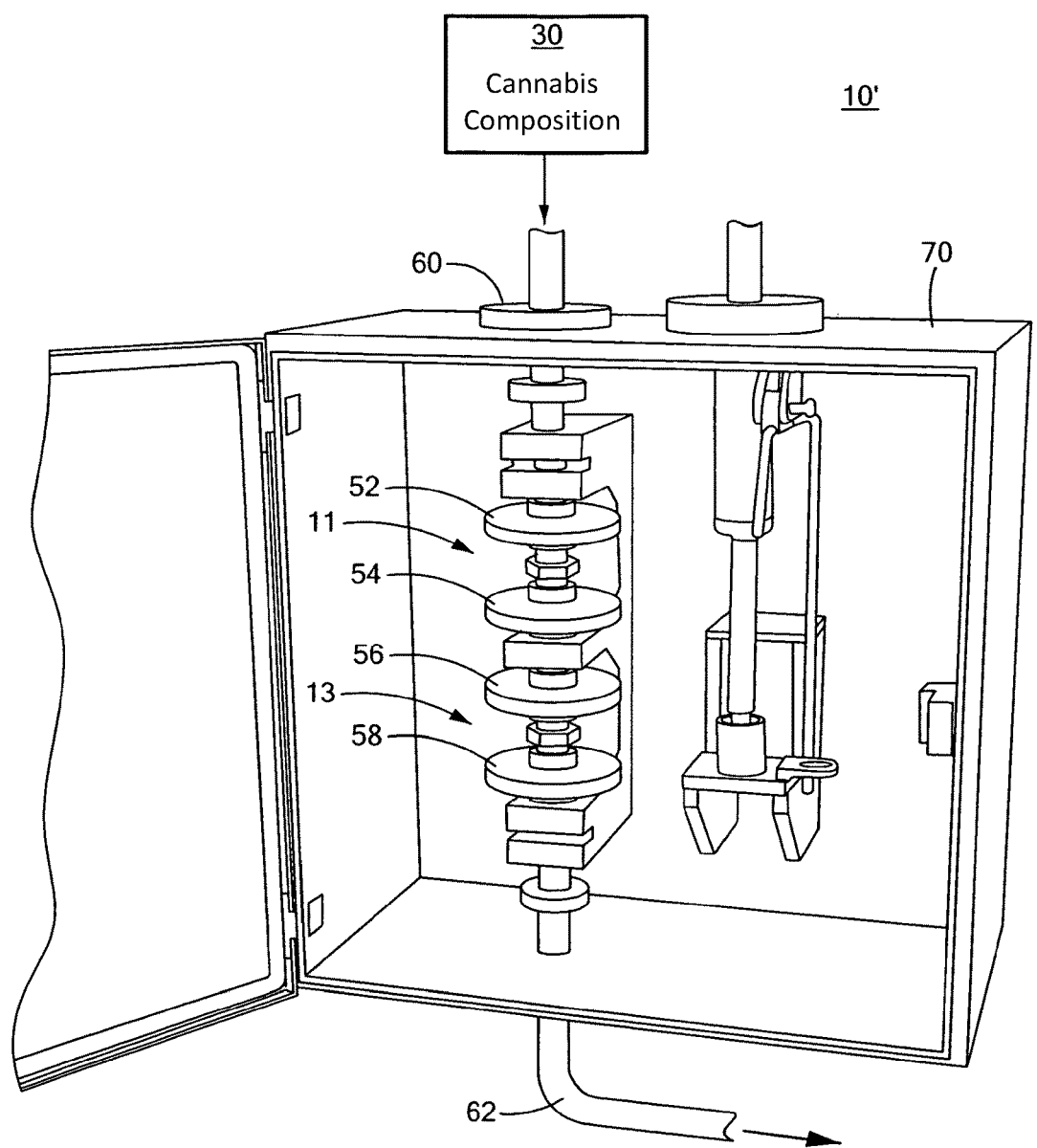
FIG. 3 depicts an example of an apparatus having a plurality of treatment chambers.

FIG. 3 depicts an example of an PEF treatment system 10' having a plurality of treatment chambers, 11 and 13, wherein each treatment chamber includes corresponding high voltage electrodes and ground electrodes coupled to a high voltage pulse modulator 32, and a high voltage DC power supply 36. The insulators between the high voltage electrodes and ground electrodes are depicted at elements 52, 54, 56, and 58. In this example, the plurality of chambers 11 and 13, are positioned within a housing 70. The chambers 11 and 13 provide four treatment zones. The cannabis composition 30 enters at inlet 60 and the processed solution including the lysate exits via outlet 62. In one example, the housing 70 is connected to a cabinet containing the high voltage pulse modulator 24 and the high voltage DC power supply 26.

Figure 4:
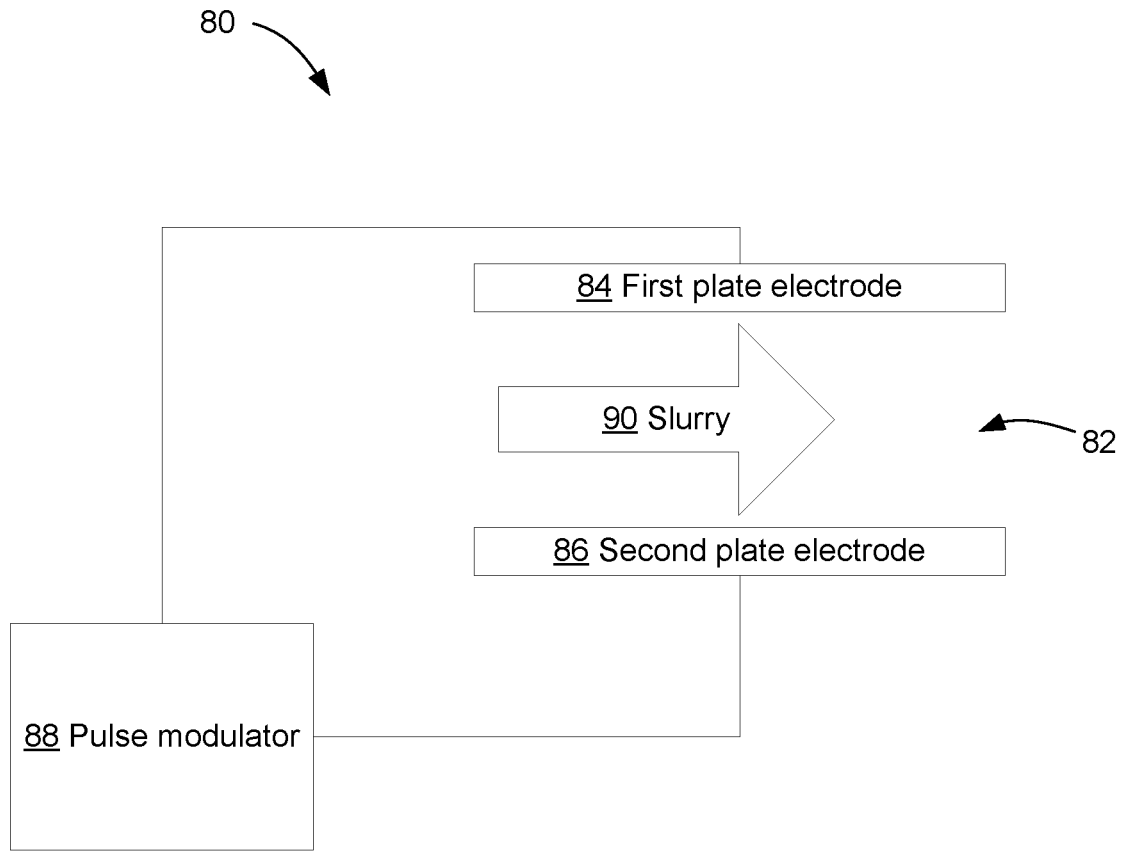
FIG. 4 depicts an example of a PEF treatment device including a treatment zone positioned between two parallel plate electrodes.

FIG. 4 depicts another example of a PEF treatment device 80. The PEF treatment device 80 includes a treatment zone 82 positioned between two parallel plate electrodes 84, 86. In this example, the two parallel plate electrodes 84, 86 are connected to a pulse modulator 88. The first plate electrode 84 may be pulsed at a positive voltage from the pulse modulator. The second plate electrode 86 may be pulsed at a negative voltage, whereby the total voltage applied during the pulse is the sum of the absolute values of the two simultaneous voltages. Alternatively, the first plate electrode 84 may be pulsed at a high voltage and the second plate electrode 86 may be grounded. The cannabis slurry composition 90 is passed between two parallel plate electrodes 84, 86 at a flow rate, and a high voltage is applied to the slurry composition 90 as it passes between the electrodes 84, 86 within the treatment zone 82. The dimensions of the electrodes, flow rate, treatment zone, etc. may be optimized to provide uniformity of the electric field between them. Other configurations of the electrodes are also possible.

Figure 5:
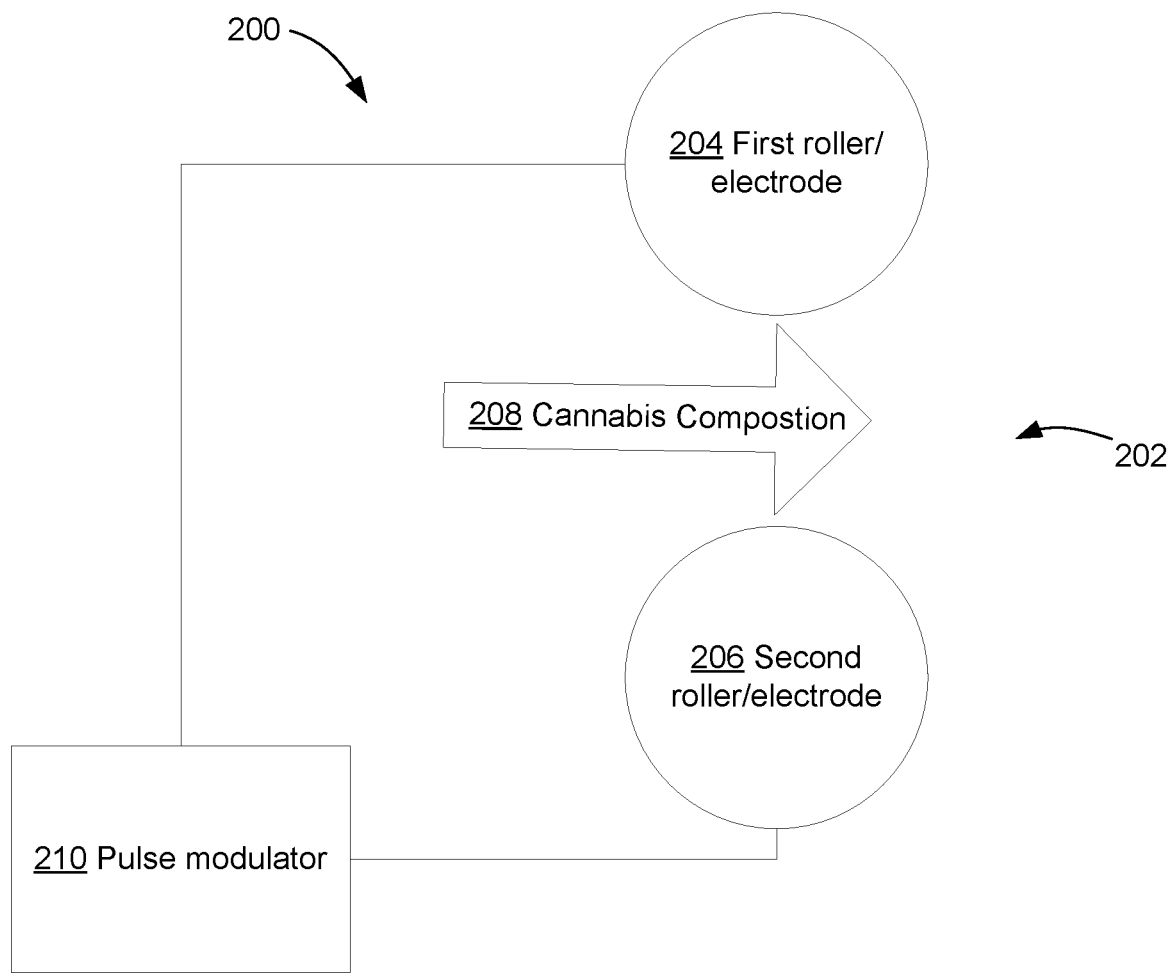
FIG. 5 depicts an example of a PEF treatment device including a treatment zone positioned between two rollers/electrodes.

FIG. 5 depicts another example of a PEF treatment device 200. The PEF treatment device 200 includes a treatment zone 202 positioned between two rollers 204, 206. The cannabis composition 208 is processed between the rollers 204, 206. The rollers 204, 206 crush the cannabis composition 208 and serve as electrodes. In other words, the rollers 204, 206 are connected to a pulse modulator 210. The first roller/electrode 204 may be pulsed at a positive voltage from the pulse modulator 210. The second roller/electrode 206 may be pulsed at a negative voltage, whereby the total voltage applied during the pulse is the sum of the absolute values of the two simultaneous voltages. Alternatively, the first roller/electrode 204 may be pulsed at a high voltage and the second roller/electrode 206 may be grounded. The cannabis composition 208 is passed between two rollers/electrodes 204, 206 at a flow rate, and a high voltage is applied to the slurry composition 208 as it passes between the rollers/electrodes 204, 206 within the treatment zone 202, at a predetermined pulse frequency chosen to achieve a desired cumulative treatment time. The distance between the rollers/electrodes, the flow rate of the cannabis composition, the electrode voltages within the treatment zone, etc., may be optimized to provide uniformity of the electric field between them. Other configurations of the rollers/electrodes are also possible.

Figure 6:
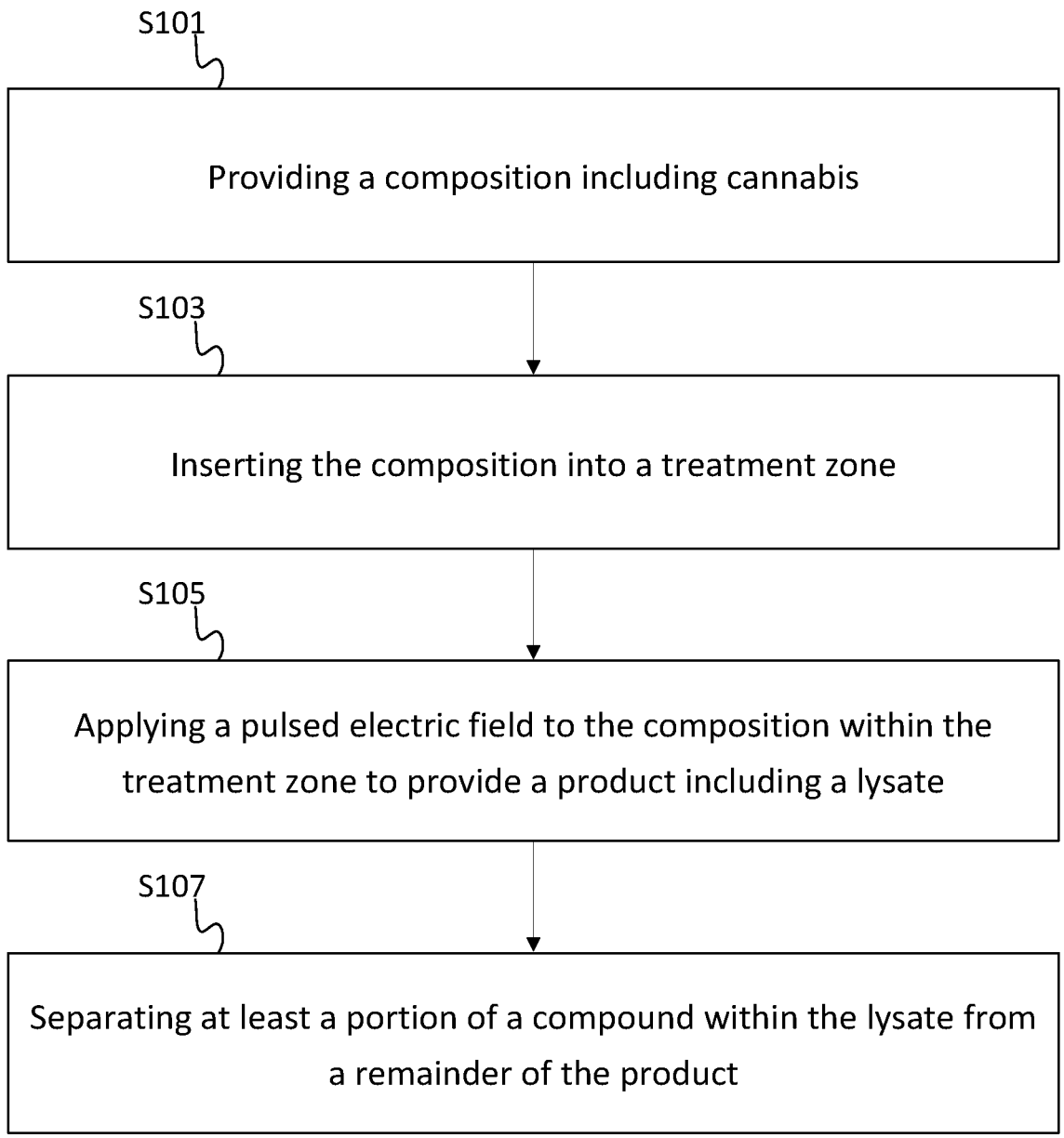
FIG. 6 depicts an example flowchart for separating compounds from cannabis.

FIG. 6 illustrates an example flowchart for separating compounds from cannabis. The process of the flowchart may be performed using the processing unit, PEF treatment device, and separation units discussed above in FIGS. 1-4. Alternatively, another device may be configured to perform one or more of the following acts. Additional, fewer, or different acts may be included.

At act S101, a composition including cannabis is provided. The composition may be a slurry composition formed by crushing the cannabis, and in some examples, adding water and/or solvent to the crushed cannabis. In some examples, the composition may be formed by freezing or chilling the cannabis plant and separating a portion of the trichomes from the frozen or chilled plant by shaking the plant to dislodge the trichomes.

At act S103, the provided cannabis composition is inserted into a treatment zone of a PEF treatment device. This may be a batch or continuous flow process.

At act S105, a pulsed electric field is applied to the cannabis composition to produce a product including a lysate. As discussed above, application of the PEF includes short (e.g., microsecond) pulses and a specialized treatment chamber to lyse the cannabis cell membranes. As noted above, the acts S101-S105 may occur at a same time, such as wherein a cannabis composition is inserted between at least two rollers that both crush the cannabis composition and subject the cannabis composition to a pulsed electric field (i.e., the rollers act as electrodes).

At act S107, at least a portion of a compound within the lysate is separated from the remainder of the product. In one example, at least a portion of the CBD is separated. In another example, at least a portion of the THC is separated. In yet another example, at least a portion of the terpenes are separated.

Other embodiments will occur to those skilled in the art and are within the following claims. One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, are apparent to those of skill in the art upon reviewing the description.

As used herein, the singular forms "a," "an," and "the" include plural referents unless the context clearly dictates otherwise.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope and spirit of the following claims and equivalents thereto are claimed as the invention.

The invention claimed is:

1. A method for separating compounds in cannabis, the method comprising:
    providing a composition comprising the cannabis;
    inserting the composition into a treatment zone;
    applying a pulsed electric field to the composition within the treatment zone, wherein a portion of cell membranes of the cannabis are lysed by electroporation to provide a product comprising a lysate, wherein a magnitude of the pulsed electric field is at least 1 kV/cm; and
    separating at least a portion of a compound within the lysate from a remainder of the product.

2. The method of claim 1, wherein the composition is a slurry composition.

3. The method of claim 2, further comprising crushing the cannabis to provide the slurry composition.

4. The method of claim 3, wherein the crushing of the cannabis is performed with at least two rollers.

5. A method for separating compounds in cannabis, the method comprising:
    providing a composition comprising the cannabis;
    inserting the composition into a treatment zone comprising at least two rollers, wherein the at least two rollers function as electrodes;
    crushing the cannabis by the at least two rollers to provide a slurry composition;
    applying a pulsed electric field to the slurry composition within the treatment zone by the at least two rollers functioning as the electrodes, wherein a portion of cell membranes of the cannabis are lysed by electroporation to provide a product comprising a lysate; and
    separating at least a portion of a compound within the lysate from a remainder of the product.

6. The method of claim 5, wherein the crushing of the cannabis and the applying of the pulsed electric field are performed at a same time.

7. The method of claim 5, further comprising:
    adding water to the crushed cannabis.

8. The method of claim 5, further comprising:
    adding at least one solvent to the crushed cannabis.

9. The method of claim 8, wherein the at least one solvent is selected from the group consisting of hexane, butane, ethanol, and combinations thereof.

10. The method of claim 2, wherein a continuous flow of the slurry composition is inserted at a flow rate of at least 1 liter/hour.

11. The method of claim 2, further comprising:
    measuring a flow rate of the slurry composition into or out of the treatment zone; and
    adjusting a frequency of the pulsed electric field based on the measured flow rate.

12. The method of claim 1, further comprising:
    separate at least a portion of trichomes of the cannabis to provide a purified composition of trichomes, wherein the composition is the purified composition of trichomes.

13. The method of claim 12, wherein the separating of the portion of the trichomes comprises:
    chilling a cannabis plant to a temperature at or below 15° C.; and
    shaking the chilled cannabis plant to separate the portion of the trichomes.

14. The method of claim 1, further comprising soaking the composition in water or a solvent prior to the inserting of the composition into the treatment zone.

15. The method of claim 1, further comprising:
    adjusting a moisture content of the composition prior to the inserting of the composition into the treatment zone.

16. The method of claim 1, further comprising:
    extracting at least a portion of unmodified cannabis from the product; and
    recycling the portion of unmodified cannabis to the treatment zone.

17. The method of claim 1, wherein a total applied pulse duration is in a range of 1 microseconds (μs) to 1 millisecond (ms).

18. The method of claim 1, further comprising:
    separating at least a portion of flower buds from the cannabis,
    wherein the composition includes the separated flower buds of the cannabis.

19. The method of claim 1, wherein the separating comprises separating at least a portion of tetrahydrocannabinol (THC) from the remainder of the product.

20. The method of claim 1, wherein the separating comprises separating at least a portion of cannabidiol (CBD) from the remainder of the product.

21. The method of claim 1, wherein the separating comprises separating at least a portion of at least one terpene from the remainder of the product.

22. The method of claim 1, wherein the magnitude of the pulsed electric field is in a range of 1 kV/cm to 10 kV/cm.

23. The method of claim 1, wherein the magnitude of the pulsed electric field is in a range of 3 kV/cm to 10 kV/cm.

24. The method of claim 1, wherein a total applied pulse duration is in a range of 0.1 microseconds (μs) to 10 milliseconds (ms).

* * * * *